(12) United States Patent
Wahl

(10) Patent No.: US 11,759,335 B2
(45) Date of Patent: *Sep. 19, 2023

(54) ENGINEERED STERILE CARTILAGE ALLOGRAFT IMPLANT PLUG WITH STERILE, SPECIFIC INSTRUMENT KIT(S)

(71) Applicant: In2Bones USA, LLC, Memphis, TN (US)

(72) Inventor: Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/010,043

(22) Filed: Sep. 2, 2020

(65) Prior Publication Data

US 2020/0397596 A1 Dec. 24, 2020

Related U.S. Application Data

(62) Division of application No. 15/048,518, filed on Feb. 19, 2016, now Pat. No. 10,779,960.

(Continued)

(51) Int. Cl.
*A61F 2/30* (2006.01)
*A61F 2/28* (2006.01)
(Continued)

(52) U.S. Cl.
CPC ........ *A61F 2/4618* (2013.01); *A61B 17/1615* (2013.01); *A61B 17/1635* (2013.01); *A61B 17/8897* (2013.01); *A61F 2/30756* (2013.01); *A61F 2/4601* (2013.01); *A61F 2/4657* (2013.01); *A61B 2090/062* (2016.02); *A61F 2/28* (2013.01); *A61F 2002/3082* (2013.01); *A61F 2002/30616* (2013.01);
(Continued)

(58) Field of Classification Search
None
See application file for complete search history.

(56) References Cited

U.S. PATENT DOCUMENTS 6,039,762 A * 3/2000 McKay ............... A61L 27/3658
606/247
6,294,187 B1 * 9/2001 Boyce ................. A61L 27/3645
424/484

(Continued)

*Primary Examiner* — Ann Schillinger
(74) *Attorney, Agent, or Firm* — Rutan & Tucker LLP; Hani Z. Sayed

(57) ABSTRACT

An apparatus and a method are provided for performing cartilage allograft implant surgeries. The apparatus comprises an allograft plug kit comprising one or more grafts configured to treat osteochondral defects in various bone joint locations in a patient's body. Each of the grafts comprises a cartilage layer coupled with a bone portion. The cartilage layer comprises a thickness selected to closely match the thickness of existing cartilage at an implant location. The bone portion comprises surface features configured to encourage the patient's bone tissue to grow into the bone portion, thereby accelerating incorporation of the graft into the patient's bone. An instrument kit comprises a multiplicity of instruments configured for implantation of the grafts into the patient's body, including at least a graft inserter, a guidewire, a reamer, and a size gauge.

13 Claims, 2 Drawing Sheets

Related U.S. Application Data

(60) Provisional application No. 62/126,053, filed on Feb. 27, 2015.

(51) Int. Cl.
*A61F 2/46* (2006.01)
*A61B 17/86* (2006.01)
*A61B 17/88* (2006.01)
*A61B 17/16* (2006.01)
*A61B 90/00* (2016.01)

(52) U.S. Cl.
CPC .............. *A61F 2002/30617* (2013.01); *A61F 2002/30805* (2013.01); *A61F 2002/4662* (2013.01); *A61F 2310/00359* (2013.01); *A61F 2310/00371* (2013.01)

(56) References Cited

U.S. PATENT DOCUMENTS

| | | | | |
|---|---|---|---|---|
| 7,981,156 B2* | 7/2011 | Pafford | ................... | A61L 27/24 623/17.11 |
| 10,779,960 B2* | 9/2020 | Wahl | .................. | A61F 2/4657 |
| 2003/0171811 A1* | 9/2003 | Steiner | ................ | A61L 27/386 623/13.17 |
| 2003/0236573 A1* | 12/2003 | Evans | ................... | A61L 31/042 623/23.58 |
| 2004/0034437 A1* | 2/2004 | Schmieding | ............ | A61L 27/52 623/20.14 |
| 2004/0230303 A1* | 11/2004 | Gomes | ................ | A61F 2/30756 623/16.11 |
| 2005/0064042 A1* | 3/2005 | Vunjak-Novakovic | ...................... | A61P 19/00 424/549 |
| 2005/0209705 A1* | 9/2005 | Niederauer | ......... | A61F 2/30756 623/23.72 |
| 2006/0200235 A1* | 9/2006 | Bianchi | ................. | A61F 2/0811 623/13.17 |
| 2006/0247790 A1* | 11/2006 | McKay | ............... | A61F 2/30756 623/23.63 |
| 2007/0073394 A1* | 3/2007 | Seedhom | ........... | A61F 2/30749 623/14.12 |
| 2007/0233135 A1* | 10/2007 | Gil | ......................... | A61F 2/4618 623/23.57 |
| 2007/0233264 A1* | 10/2007 | Nycz | ..................... | A61F 2/0095 623/23.57 |
| 2007/0270711 A1* | 11/2007 | Gil | ..................... | A61B 17/1635 600/567 |
| 2008/0077251 A1* | 3/2008 | Chen | .................... | A61F 2/4644 623/23.72 |
| 2008/0262616 A1* | 10/2008 | McKay | ...................... | A61F 2/28 623/14.12 |
| 2009/0054906 A1* | 2/2009 | Walthall | ................ | A61F 2/4618 606/108 |
| 2009/0291112 A1* | 11/2009 | Truncale | .................. | A61L 27/48 424/549 |
| 2009/0312842 A1* | 12/2009 | Bursae | ................ | A61F 2/30771 623/23.72 |
| 2009/0319045 A1* | 12/2009 | Truncale | ................. | A61L 27/48 623/23.73 |
| 2010/0274355 A1* | 10/2010 | McGuire | ............... | A61F 2/0811 623/13.14 |
| 2014/0243836 A1* | 8/2014 | Bake | .................... | A61F 2/4618 606/88 |
| 2014/0316531 A1* | 10/2014 | Klinger | ................. | A61F 2/3603 623/23.12 |
| 2016/0081807 A1* | 3/2016 | Estes | ................... | A61F 2/30756 623/14.12 |
| 2019/0328548 A1* | 10/2019 | Bake | .................... | A61F 2/4684 |

* cited by examiner

ENGINEERED STERILE CARTILAGE ALLOGRAFT IMPLANT PLUG WITH STERILE, SPECIFIC INSTRUMENT KIT(S)

PRIORITY

This application claims the benefit of and priority to U.S. patent application Ser. No. 15/048,518 filed on Feb. 19, 2016 and U.S. Provisional Application, entitled "Engineered Sterile Cartilage Allograft Implant Plug With Sterile, Specific Instrument Kit(s)," filed on Feb. 27, 2015 having application Ser. No. 62/126,053.

FIELD

The field of the present disclosure generally relates to surgical implants. More particularly, the field of the invention relates to an apparatus and a method for performing cartilage allograft implant surgeries to repair osteochondral defects.

BACKGROUND

Articular cartilage is a smooth, white tissue which covers the ends of bones where they come together to form joints in humans and many animals so as to facilitate articulation of the joints and protect and cushion the bones. Cartilage may become damaged, however, due to abrupt trauma or prolonged wear. A number of surgical techniques have been developed to treat damaged cartilage. Restoring articular cartilage is known to relieve pain and facilitate better joint function, as well as potentially delaying or preventing an onset of arthritis. One surgical technique comprises transplantation of a healthy osteochondral allograft so as to replace damaged cartilage and encourage new cartilage growth.

During an osteochondral allograft transplantation, an allograft plug, often referred to as an osteochondral plug or core, is harvested from a condyle or rounded joint-forming portion of a donor bone. Typically, the allograft plug comprises a portion of bone with a healthy cartilage on the surface. In some cases, the allograft plug may also include an attached portion of cancellous tissue, which is the porous inner material that is present in many bones. During the transplant procedure, damaged cartilage is removed and a portion of bone is cut away and removed from the joint, thereby forming an osteochondral hole or bore. The allograft plug is then inserted into the osteochondral bore and attached such that the healthy cartilage of the allograft plug aligns with the cartilage on the surface of the bone joint being treated.

What is needed, however, is a kit which enables a surgeon to select specifically-sized allograft plugs and corresponding surgical implantation tools so as to improve the accuracy and simplicity of osteochondral allograft transplantation surgeries.

SUMMARY

An apparatus and a method are provided for performing cartilage allograft implant surgeries. The apparatus comprises an allograft plug kit comprising one or more grafts configured to treat osteochondral defects in various bone joint locations in a patient's body. Each of the grafts comprises a cartilage layer coupled with a bone portion, and has a diameter and a length suitable for the bone joint location to be treated. In one embodiment, the grafts comprise diameters ranging from substantially 5 millimeters (mm) to substantially 15 mm, and each of the grafts has a length of substantially 12 mm. The cartilage layer comprises a thickness selected to closely match the thickness of existing cartilage at an implant location. The bone portion comprises surface features configured to encourage the patient's bone tissue to grow into the bone portion, thereby accelerating incorporation of the graft into the patient's bone. An instrument kit comprises a multiplicity of instruments configured for implantation of the grafts into the patient's body, including at least a graft inserter, a guidewire, a reamer, and a size gauge.

In an exemplary embodiment, an apparatus for performing cartilage allograft implant surgeries comprises a sterile allograft plug kit comprising one or more grafts configured to treat osteochondral defects in various bone joint locations in a patient's body, the one or more grafts each comprising a cartilage layer coupled with a bone portion; and at least one sterile instrument kit comprising a multiplicity of instruments including at least a graft inserter, a guidewire, a reamer, and a size gauge, the multiplicity of instruments being configured for implanting the one or more grafts into the patient's body.

In another exemplary embodiment, the graft inserter comprises an elongate member having a distal graft retainer and a proximal applicator, the distal graft retainer comprising an opening configured to receive and hold the graft, the proximal applicator being in mechanical communication with the distal graft retainer by way of an interior channel of the elongate member whereby the proximal applicator may be used to push the graft out of the distal graft retainer and into an osteochondral bore in the patient's body. In another exemplary embodiment, the graft inserter comprises a viewport and a graft length indicator, the viewport facilitating direct observation of the graft within the distal graft retainer, the graft length indicator comprising a series of ring lines positioned adjacent to the viewport with a sequentially increasing distance from the distal graft retainer. In another exemplary embodiment, when the graft is fully received into the distal graft retainer, the position of the top of the cartilage layer relative to the graft length indicator provides a visual indication of a total length of the graft.

In another exemplary embodiment, the guidewire comprises an elongate shaft having a distal pointed tip and a proximal blunt end, wherein the distal pointed tip is configured to advance through obstructive tissues and structures within bone joints, and wherein the proximal blunt end facilitates manipulation of the guidewire by hand. In another exemplary embodiment, the guidewire is comprised of a surgical stainless steel.

In another exemplary embodiment, the reamer comprises a rigid elongate shaft having a distal cutting end and a proximal shank, the distal cutting end comprising a cutting edge suitable for rotatably clearing an osteochondral bore, and the proximal shank being configured to be grasped by a chuck of a surgical drill, or other equivalent rotary tool. In another exemplary embodiment, the distal cutting edge comprises a spiral cutting edge. In another exemplary embodiment, the reamer comprises a central, lengthwise hole whereby the reamer is mountable onto the guidewire so as to direct the distal cutting end to an implant location within the bone joint.

In another exemplary embodiment, the size gauge comprises an elongate member having a depth indicator and a proximal handle portion, the depth indicator comprising a series of ring lines positioned on the elongate member with a sequentially increasing distance from a distal end of the size gauge, the ring lines being configured to indicate the depth of an osteochondral bore into which the distal end is inserted. In another exemplary embodiment, the depth indicator correlates with a graft length indicator of the graft inserter so as to enable a surgeon to ensure that the osteochondral bore is drilled to a depth suitable to receive the graft. In another exemplary embodiment, the elongate member comprises a central, lengthwise hole having a diameter suitable to receive the guidewire so as to direct the depth indicator to the osteochondral bore.

In another exemplary embodiment, the one or more grafts comprise diameters ranging from substantially 5 millimeters (mm) to substantially 15 mm, and each of the one or more grafts comprises a length of substantially 12 mm. In another exemplary embodiment, the one or more grafts are each harvested as a one-piece component from a bone joint location in a cadaver. In another exemplary embodiment, the cartilage layer comprises a thickness which closely matches a thickness of existing cartilage at an implant location.

In another exemplary embodiment, the bone portion comprises a multiplicity of surface features configured to encourage the patient's bone tissue to grow into the bone portion, thereby accelerating incorporation of the graft into the patient's bone. In another exemplary embodiment, the surface features comprise holes, dimples, or circumferentially distributed longitudinal grooves. In another exemplary embodiment, the holes comprise diameters depending upon the size of the grafts and the locations within the patient's body where the grafts are intended to be implanted. In another exemplary embodiment, the longitudinal grooves may be implemented with a variety of widths, lengths, depths and cross-sectional shapes within the bone portion.

In an exemplary embodiment, a method for an instrument kit for implanting grafts into bone joints of a patient comprises configuring one or more grafts to treat osteochondral defects in various bone joint locations in the patient's body, the one or more grafts each comprising a cartilage layer coupled with a bone portion; assembling the one or more grafts into a sterile allograft plug kit, the one or more grafts having different diameters that are suitable for the various bone joint locations in the patient's body; and combining the sterile allograft plug kit with a multiplicity of instruments configured for implantation of the one or more grafts into the patient's body, the multiplicity of instruments including at least a graft inserter, a guidewire, a reamer, and a size gauge. In another exemplary embodiment, configuring comprises forming the one or more grafts such that the diameters of the one or more grafts range from substantially 5 mm to substantially 15 mm.

BRIEF DESCRIPTION OF THE DRAWINGS

The drawings refer to embodiments of the present disclosure in which.

Figure 1:
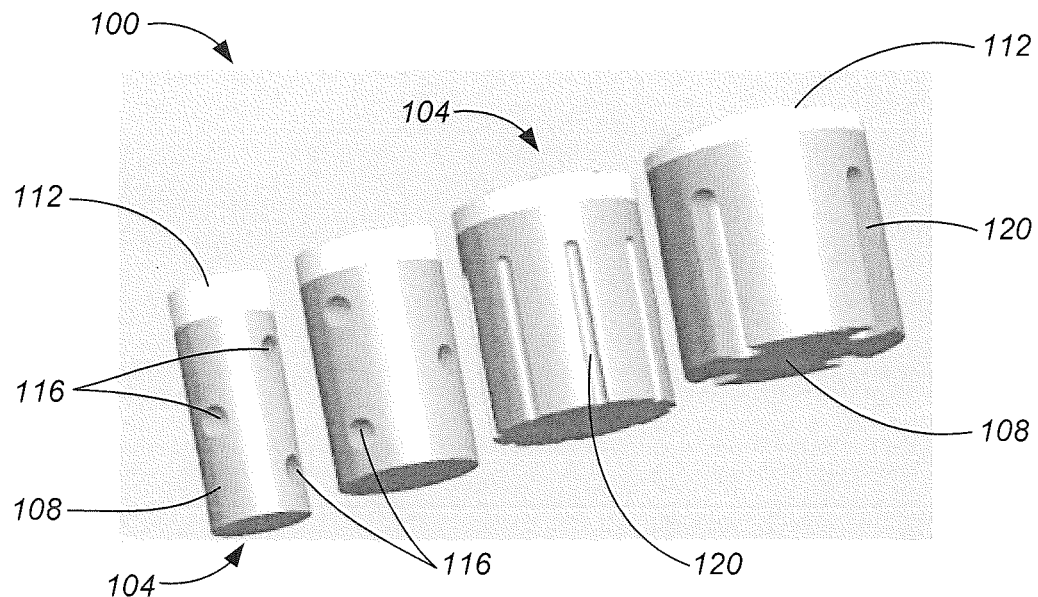
FIG. 1 illustrates a lower perspective view of an exemplary embodiment of an allograft plug kit, according the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first graft," may be made. However, the specific numeric reference should not be interpreted as a literal sequential order but rather interpreted that the "first graft" is different than a "second graft." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for performing cartilage allograft implant surgeries. The apparatus comprises an allograft plug kit comprising one or more grafts configured to treat osteochondral defects in various bone joint locations in a patient's body. The grafts each comprise a cartilage layer coupled with a bone portion. The cartilage layer comprises a thickness which closely matches the thickness of existing cartilage at an implant location. The bone portion comprises surface features configured to encourage the patient's bone tissue to grow into the bone portion, thereby accelerating incorporation of the graft into the patient's bone. In some embodiments, the grafts comprise diameters ranging from substantially 5 millimeters (mm) to substantially 15 mm, and each of the grafts comprises a length of substantially 12 mm. An instrument kit comprises a multiplicity of instruments including at least a graft inserter, a guidewire, a reamer, and a size gauge. The instruments are configured for implantation of the grafts into the patient's body. In some embodiments, the graft inserter comprises an elongate member having a distal graft retainer and a proximal applicator. The distal graft retainer includes an opening configured to receive and hold the graft. The proximal applicator facilitates pushing the graft out of the distal graft retainer and into an osteochondral bore formed in a bone joint of the patient.

Figure 2:
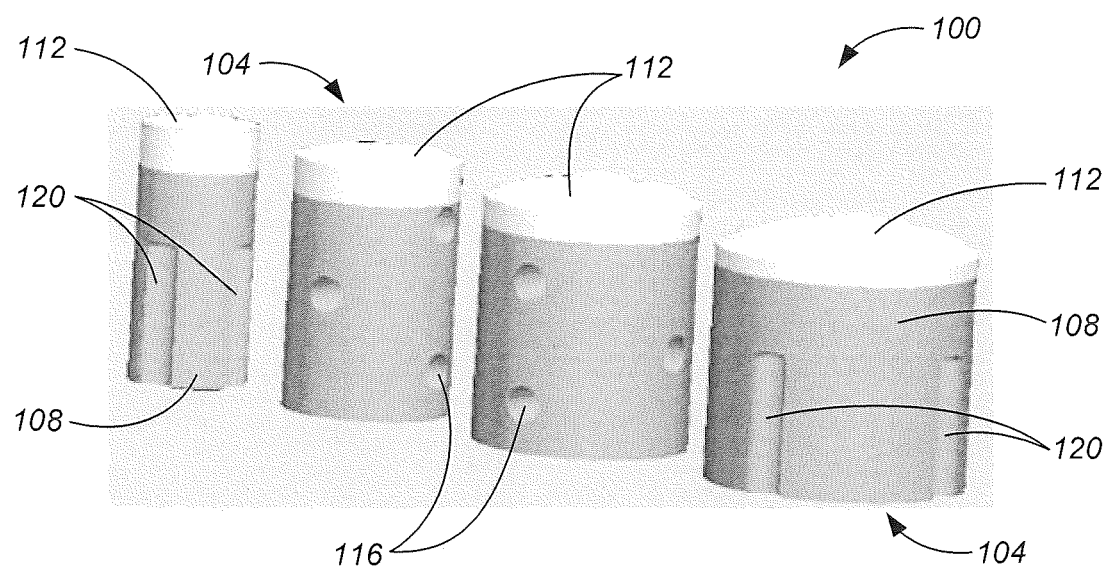
FIG. 2 illustrates an upper perspective view of an exemplary embodiment of an allograft plug kit in accordance with the present disclosure.

FIGS. 1 and 2 illustrate respective lower and upper perspective views of exemplary embodiments of an allograft plug kit 100 advantageously configured for repairing a wide range of osteochondral defects, according the present disclosure. The allograft plug kit 100 generally comprises a multiplicity of grafts 104 ranging from a relatively small diameter to a relatively large diameter. It will be appreciated that the range in diameters facilitates using the allograft plug kit 100 to treat osteochondral defects in various bone joint locations in the human body, such as by way of non-limiting example, a femoral condyle (most common), a humeral head, a talus, a capitellum of the elbow, and the like.

In the exemplary embodiments illustrated in FIGS. 1 and 2, the allograft plug kit 100 comprises four grafts 104 ranging in size from substantially 5 millimeters (mm) in diameter to substantially 15 mm in diameter. In some embodiments, the allograft plug kit 100 may comprise a number of grafts greater than four, and thus grafts having diameters smaller than 5 mm and/or greater than 15 mm may be included in the allograft plug kit 100. Moreover, the grafts 104 in the embodiments illustrated in FIGS. 1 and 2 each comprises a length of substantially 12 mm. In some embodiments, however, the grafts 104 may comprise different lengths, depending upon the particular bone joints for which the grafts 104 are intended. In some embodiments, the lengths of the grafts 104 may range from a relatively small value to a relatively large value. In some embodiments, the length of each graft 104 may be configured to correlate with the diameter of the graft. It will be appreciated that the allograft plug kit 100 advantageously provides specifically-sized grafts 104 whereby a surgeon may select the grafts based on a particular bone joint to be treated. Further, it should be understood that a wide variety of dimensions and sizes of the grafts 104 may be incorporated into the allograft plug kit 100 without deviating from the spirit and scope of the present disclosure.

As further illustrated in FIGS. 1 and 2, each of the grafts 104 comprises a bone portion 108 and a cartilage layer 112. It will be appreciated that each of the grafts 104 preferably is harvested as a one-piece component from a cartilage/bone joint location in a cadaver, and thus the cartilage layer 112 is advantageously affixed to the bone portion 108. It will be recognized by those skilled in the art that during implantation of the graft 104 into a recipient patient, damaged cartilage and underlying bone is removed from a joint to be treated, thereby forming an osteochondral bore having a diameter advantageously sized to receive the graft 104. The graft 104 is then inserted into the bore such that the surface of the cartilage layer 112 is aligned with the surrounding cartilage, thus encouraging healing and incorporation of the graft 104 into the patient's joint. As such, the cartilage layer 112 preferably comprises a thickness which closely matches the thickness of the existing cartilage in the patient's joint. In some embodiments, the cartilage layer 112 comprises a thickness which depends upon the location in the cadaver from where the graft 104 is harvested. In some embodiments, the cartilage layer 112 is roughly 2 mm in thickness.

The bone portion 108 further comprises a multiplicity of surface features configured so as to promote the recipient patient's bone tissue to grow into the bone portion 108, thereby accelerating incorporation of the graft 104 into the patient's bone. In the embodiments illustrated in FIGS. 1 and 2, the surface features comprise holes 116 and longitudinal grooves 120. In some embodiments, the holes 116 may be relatively shallow so as to form dimples on the sides of the bone portion 108. In some embodiments, the holes 116 may be relatively deep, or extend all the way across the diameter of the bone portion 108. Further, various diameter sizes of the holes 116 may be implemented depending upon the size of the grafts 104 and the locations within the patient's body for which the grafts 104 are intended to be implanted.

Similarly, the longitudinal grooves 120 may be implemented with a variety of widths, lengths, and depths within the bone portion 108. Moreover, any number of the longitudinal grooves 120 may be formed into the bone portion 108 and distributed around the circumference of the graft 104. As will be appreciated, the specific number and dimensions of the longitudinal grooves 120 may be implemented based on the sizes of the grafts 104 and the locations within the patient's body where the grafts 104 are to be implanted.

Further, the longitudinal grooves 120 may be implemented with a wide variety of cross-sectional shapes. In some embodiments, the longitudinal grooves 120 comprise a hemispherical cross-sectional shape. In some embodiments, the longitudinal grooves 120 comprise a rectangular cross-sectional shape. In some embodiments, the longitudinal grooves 120 comprise a triangular, or wedge, cross-sectional shape. Moreover, the longitudinal grooves 120 incorporated into an individual graft 104 are not limited to possessing the same cross-sectional shape, but rather various cross-sectional shapes may be applied to the longitudinal grooves 120 formed on each individual graft 104. It should be understood, therefore, that individual grafts 104 need not be limited to one type of surface feature, but rather different types of surface features may be mixed incorporated into each of the grafts 104. Further, surface features other than holes and longitudinal grooves, as may become apparent to those skilled in the art, may be incorporated into the grafts 104 without going beyond the scope of the present disclosure.

Figure 3:
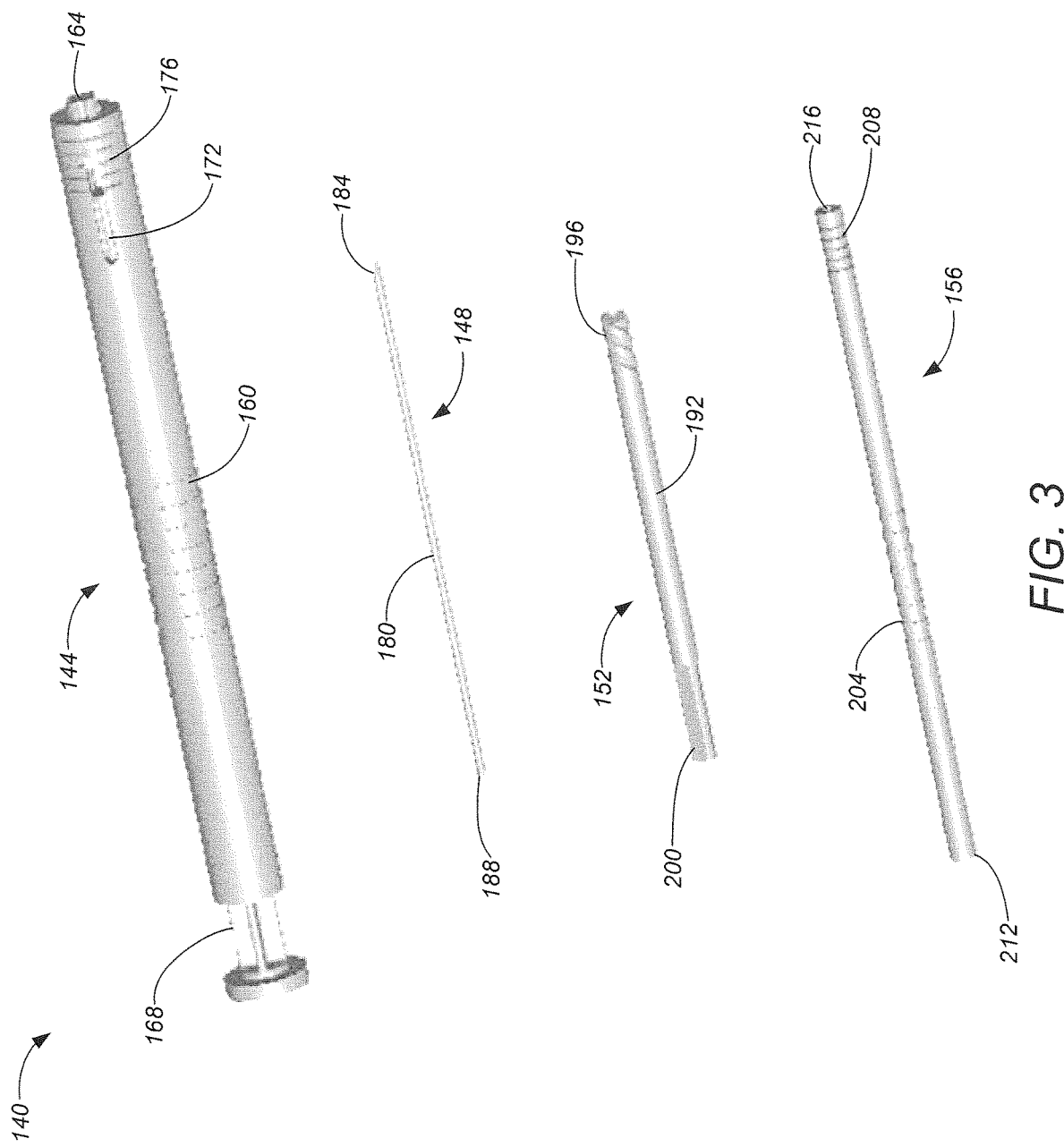
FIG. 3 illustrates a perspective view of an exemplary embodiment of a sterile instrument kit for implanting allograft plugs into bone joints of a patient in accordance with the present disclosure.

FIG. 3 illustrates a perspective view of an exemplary embodiment of an instrument kit 140 configured for implanting the grafts 104 into bone joints of a patient, as described herein. In the embodiment illustrated in FIG. 3, the instrument kit 140 comprises a graft inserter 144, a guidewire 148, a reamer 152, and a size gauge 156. In some embodiments, the instrument kit 140 may further comprise a tamp (not shown). As will be appreciated, the instrument kit 100 comprises instruments necessary to perform cartilage allograft implant surgeries. The sizes of the instruments comprising the kit 140 will depend upon the size of the particular graft 104 to be implanted into the patient. It is envisioned, therefore, that a surgeon may select one or more of the grafts 104 and a correspondingly sized embodiment of the instrument kit 140 based on the location and size of the bone joint to be treated.

Referring still to FIG. 3, the graft inserter 144 comprises a generally elongate member 160 having a distal graft retainer 164 and a proximal applicator 168. The proximal applicator 168 is in mechanical communication with the distal graft retainer 164 by way of an interior channel of the elongate member 160. The distal graft retainer 164 comprises an opening configured to receive and advantageously hold the graft 104 while the graft inserter 144 is used to direct the graft 104 to an implant location within the patient. As will be appreciated, the implant location generally is a surgically performed osteochondral bore formed so as to remove damaged articular cartilage and a portion of the underlying bone tissue so as to accommodate implantation of the graft 104. As such, the osteochondral bore has a diameter and a depth suitable to receive the graft 104, such that the cartilage layer 112 aligns with surrounding healthy cartilage in the bone joint. Once the graft 104 is suitably positioned at the implant location, the proximal applicator 168 may be used to push the graft 104 out of the distal graft retainer 164 and into the osteochondral bore.

A viewport 172 facilitates directly observing the position of the graft 104 within the distal graft retainer 164. Further, the viewport 172 facilitates observing the length of the graft by way of a graft length indicator 176. The graft length indicator 176 comprises a series of ring lines positioned adjacent to the viewport 172 with a sequentially increasing distance from the distal graft retainer 164. As will be appreciated, when the graft 104 is fully received into the distal graft retainer 164, the position of the top of the cartilage layer 112 relative to the graft length indicator 176 provides a visual indication of the total length of the graft 104. Thus, the viewport 172 and the graft length indicator 176 advantageously enables the surgeon to verify that a correctly sized graft 104 has been selected for surgery.

As illustrated in FIG. 3, the guidewire 148 comprises an elongate shaft 180 having a distal pointed tip 184 and a proximal blunt end 188. The guidewire 148 is configured to be inserted into confined spaces within bone joints and serves to direct a subsequent insertion of the reamer 152 and the size gauge 156 to the implant location within the bone joint. In some embodiments, the guidewire 148 is comprised of a surgical stainless steel, such as austenitic 316 stainless steel, martensitic 440 stainless steel, martensitic 420 stainless steel, and the like. It will be appreciated that the distal pointed tip 184 facilitates advancing the guidewire 148 through obstructive tissues and structures, and the proximal blunt end 188 facilitates manipulating the guidewire 148 by hand, or by way of an appropriate tool.

The reamer 152 comprises a rigid elongate shaft 192 having a distal cutting end 196 and a proximal shank 200. The distal cutting end 196 comprises a cutting edge suitable for rotatably clearing an osteochondral bore, thereby removing damaged articular cartilage and an underlying bone portion from the bone joint being treated. In some embodiments, the distal cutting edge 196 comprises a spiral cutting edge, although other suitable cutting edge configurations will be apparent. The proximal shank 200 is configured to be grasped by a chuck of a surgical drill, or other equivalent rotary tool. Further, in some embodiments the reamer 152 comprises a central, lengthwise hole whereby the reamer may be mounted onto the guidewire 148 so as to direct the distal cutting end 196 to the implant location within the bone joint.

Within continuing reference to FIG. 3, the size gauge 156 comprises a generally elongate member 204 having a depth indicator 208 and a proximal handle portion 212. The size gauge 156 further comprises a central, lengthwise hole 216 having a diameter suitable to receive the guidewire 148. The central hole 216 facilitates mounting the size gauge onto the guidewire 148 so as to direct the depth indicator 208 to the osteochondral bore formed within the bone joint. The depth indicator 208 comprises a series of ring lines positioned on the elongate member with a sequentially increasing distance from a distal end of the size gauge 156. As will be appreciated, upon inserting the depth indicator 208 fully into the osteochondral bore, the ring lines provide the surgeon with a direct observation of the depth of the bore. It should be understood that the depth indicator 208 generally correlates with the graft length indicator 176 of the graft inserter 144 so as to ensure that the osteochondral bore is drilled to a depth suitable to accommodate the graft 104, such that the cartilage layer 112 aligns with the surrounding cartilage within the bone joint.

It is envisioned that the instrument kit 140 is to be suitably sterilized for surgeries, and packaged into sterilized containers. In some embodiments, the size gauge 156 is packaged in a first sterile container, while the graft inserter 144, the guidewire 148, and the reamer 152 are packaged in a second sterile container, and the graft 104 is packaged in a third sterile container. The first, second, and third sterile containers are then bundled together into a single, exterior container, thereby forming a convenient surgery-specific cartilage allograft package. It is envisioned that other packaging techniques will be apparent to those skilled in the art without deviating from the spirit and scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. An apparatus for performing cartilage allograft implant surgeries, comprising:
    a sterile allograft plug kit comprising one or more grafts configured to treat osteochondral defects in various bone joint locations in a patient's body, the one or more grafts each comprising a cartilage layer having a thickness of approximately 2 mm coupled with a bone portion;
    at least one sterile instrument kit comprising a multiplicity of instruments including at least a graft inserter, a guidewire, a reamer, and a size gauge, the multiplicity of instruments being configured for implanting the one or more grafts into the patient's body;
    wherein the bone portion comprises a multiplicity of surface features comprising at least four circumferentially distributed longitudinal grooves that extend into the bone portion and terminate before the cartilage layer and features a hemispherical or rectangular cross-sectional shape;
    wherein the surface features are configured to encourage the patient's bone tissue to grow into the bone portion, thereby accelerating incorporation of the graft into the patient's bone; and
    wherein the graft inserter comprises a viewport and a graft length indicator, the viewport facilitating direct observation of the graft within the distal graft retainer; the graft length indicator comprising:
    a series of ring lines positioned adjacent to the viewport with a sequentially increasing distance from the distal graft retainer; and
    wherein when the graft is fully received into the distal graft retainer, the position of the top of the cartilage layer relative to the graft length indicator provides a visual indication of a total length of the graft.

2. The apparatus of claim 1, wherein the graft inserter comprises an elongate member having a distal graft retainer and a proximal applicator, the distal graft retainer comprising an opening configured to receive and hold the graft, the proximal applicator being in mechanical communication with the distal graft retainer by way of an interior channel of the elongate member whereby the proximal applicator may be used to push the graft out of the distal graft retainer and into an osteochondral bore in the patient's body.

3. The apparatus of claim 1, wherein the guidewire comprises an elongate shaft having a distal pointed tip and a proximal blunt end, wherein the distal pointed tip is configured to advance through obstructive tissues and structures within bone joints, and wherein the proximal blunt end facilitates manipulation of the guidewire by hand.

4. The apparatus of claim 3, wherein the guidewire is comprised of a surgical stainless steel.

5. The apparatus of claim 1, wherein the reamer comprises a rigid elongate shaft having a distal cutting end and a proximal shank, the distal cutting end comprising a cutting edge suitable for rotatably clearing an osteochondral bore, and the proximal shank being configured to be grasped by a chuck of a surgical drill.

6. The apparatus of claim 5, wherein the distal cutting edge comprises a spiral cutting edge.

7. The apparatus of claim 5, wherein the reamer comprises a central, lengthwise hole whereby the reamer is mountable onto the guidewire so as to direct the distal cutting end to an implant location within the bone joint.

8. The apparatus of claim 1, wherein the size gauge comprises an elongate member having a depth indicator and a proximal handle portion, the depth indicator comprising a series of ring lines positioned on the elongate member with a sequentially increasing distance from a distal end of the size gauge, the ring lines being configured to indicate the depth of an osteochondral bore into which the distal end is inserted.

9. The apparatus of claim 8, wherein the depth indicator correlates with a graft length indicator of the graft inserter so as to enable a surgeon to ensure that the osteochondral bore is drilled to a depth suitable to receive the graft.

10. The apparatus of claim 8, wherein the elongate member comprises a central, lengthwise hole having a diameter suitable to receive the guidewire so as to direct the depth indicator to the osteochondral bore.

11. The apparatus of claim 1, wherein the one or more grafts comprise diameters ranging from substantially 5 millimeters (mm) to substantially 15 mm, and each of the one or more grafts comprises a length of substantially 12 mm.

12. The apparatus of claim 1, wherein the one or more grafts are each harvested as a one-piece component from a bone joint location in a cadaver.

13. The apparatus of claim 12, wherein the cartilage layer comprises a thickness which matches a thickness of existing cartilage at an implant location.

\* \* \* \* \*